(12) United States Patent
Cohen

(10) Patent No.: US 9,615,732 B2
(45) Date of Patent: Apr. 11, 2017

(54) DENTAL MIRROR COVER

(76) Inventor: Jeff Cohen, Arlington, VA (US)

(*) Notice: Subject to any disclaimer, the term of this patent is extended or adjusted under 35 U.S.C. 154(b) by 1321 days.

(21) Appl. No.: 13/192,680

(22) Filed: Jul. 28, 2011

(65) Prior Publication Data

US 2013/0029287 A1    Jan. 31, 2013

(51) Int. Cl.
*A61B 1/24*      (2006.01)
*A61B 1/247*    (2006.01)

(52) U.S. Cl.
CPC .................................. *A61B 1/247* (2013.01)

(58) Field of Classification Search
CPC ........................................................ A61B 1/247
USPC ...... 433/29–31, 141; 359/852; 600/246, 247
See application file for complete search history.

(56) References Cited

U.S. PATENT DOCUMENTS

| | | | |
|---|---|---|---|
| 751,950 A * | 2/1904 | Sharp | ................................ 433/30 |
| 1,067,571 A | 7/1913 | Abbott | |
| 2,140,005 A | 12/1938 | Greenberg | |
| 2,606,366 A | 8/1952 | Stevens | |
| 2,656,559 A | 10/1953 | Wiseman | |
| 2,752,682 A | 7/1956 | Wiseman | |
| 3,829,199 A * | 8/1974 | Brown | ........................... 359/882 |
| 4,512,635 A * | 4/1985 | Melde | ............................ 359/882 |
| 4,757,381 A * | 7/1988 | Cooper et al. | .................... 348/66 |
| 4,859,180 A | 8/1989 | Smith et al. | |
| 5,197,875 A | 3/1993 | Nerli | |
| 5,265,720 A * | 11/1993 | Meliconi | ........................ 206/305 |
| 5,338,195 A | 8/1994 | Flannagan | |
| 5,490,781 A | 2/1996 | Wade | |
| 6,048,202 A | 4/2000 | Jensen et al. | |
| 6,315,565 B1 | 11/2001 | Slotke et al. | |
| 6,382,972 B1 | 5/2002 | Fischer et al. | |
| 6,666,682 B1 * | 12/2003 | Meyerhof | ......................... 433/31 |
| 7,927,100 B2 | 4/2011 | Euvrard et al. | |
| 2009/0042161 A1* | 2/2009 | Jodaikin et al. | ................. 433/80 |
| 2010/0304324 A1 | 12/2010 | Dragan et al. | |
| 2011/0183107 A1* | 7/2011 | Wickman-Dykes | ........... 428/131 |

FOREIGN PATENT DOCUMENTS

| | | |
|---|---|---|
| CN | 86 2 06737 U | 8/1987 |
| EP | 0 282 832 A1 | 9/1988 |
| GB | 1 278 943 A | 6/1972 |

* cited by examiner

*Primary Examiner* — Heidi M Eide
(74) *Attorney, Agent, or Firm* — Millen White Zelano & Branigan, P.C.

(57) ABSTRACT

A device for covering dental mirrors to prevent contact of metal surfaces of a dental mirror from coming in to contact with a persons mouth while in use without covering the mirror portion of the mouth mirror.

9 Claims, 3 Drawing Sheets

DENTAL MIRROR COVER

FIELD OF INVENTION

The invention relates to covers for dental mirrors.

BACKGROUND OF THE INVENTION

Dental mirrors typically have a frame (6) composed of metal or which feels unpleasant when in contact with the teeth, gums, cheek, or tongue. Contact with the teeth can also produce an unpleasant clicking sound. Efforts to lessen the discomfort produced by dental mirrors have been made. U.S. Pat. No. 4,859,180 employs a soft absorbent roller at the top of the dental mirror to help prevent contact of the mirror with the mouth. U.S. Pat. No. 6,666,682 uses a rubber bumper along the sides of the mirror to prevent the mirror from contacting the mouth, particularly, the teeth. None of these built in solutions provide complete protection for the mouth and also fail to provide a way of retrofitting dental mirrors already in use. There is therefore a need to retro fit dental mirrors now in use and provide complete protection for the mouth.

SUMMARY OF THE INVENTION

The invention is a device that acts as a jacket or cover for a dental mirror. The device is composed of a soft elastic material, preferably rubber or silicone, and fits over and around the frame (6) holding the dental mirror to handle (5) and extends slightly over the edges of the front face of the mirror. Once the device has been fitted on to the dental mirror, the frame (6) of the mirror is completely covered and the portion of the device extending slightly from the front face of the dental mirror reduces the likelihood of the mirror portion of the dental mirror coming in contact with the mouth without reducing or minimally reducing the reflection provided by the mirror portion of the dental mirror.

For the purposes of this invention a dental mirror refers to those ordinarily used in the art which are generally comprised of a handle (5) and a head where the head comprises a frame (6) and a mirror. On the front face of the head is the mirror and the sides and back of the head constitute the frame (6) which connects to the handle (5) and holds the mirror to the device. The head is generally circular in shape and has a flat back and face. In some embodiments, the head can be different shapes for example a square, rectangle, oval, or triangle. The sides are generally curved or straight.

The invention is a device for covering the back and sides of dental mirrors which have a generally round and planar back portion and a curved side portion. The side portion is capable of wrapping around the sides of a dental mirror and securing said cover to said dental mirror.

In some embodiments the back and side portions of the device are comprised of soft elastic material. The soft elastic material is, for example, rubber, latex, or silicone.

In some embodiments of the device, the entire back and sides of the dental mirror is covered.

In some embodiments of the device at least 90% of the front face of the dental mirror is uncovered.

In some embodiments, the device can be sterilized without losing its shape.

In some embodiments, the bottom portion extends the entire length of the handle (5) of the dental mirror.

In some embodiments, the entire mirror portion of the dental mirror is left uncovered by the device. In these embodiments there is optionally no front portion. Where a part of the frame (6) occupies a portion of the front face of the dental mirror the device may optionally have a front portion that covers this part of the frame (6) but no portion of the mirror.

In some embodiments the device is antimicrobial. The device may be made of materials with antimicrobial properties or a non-toxic antimicrobial coating may be applied to the device without impacting its use.

DETAILED DESCRIPTION OF THE DRAWINGS

Figure 1:
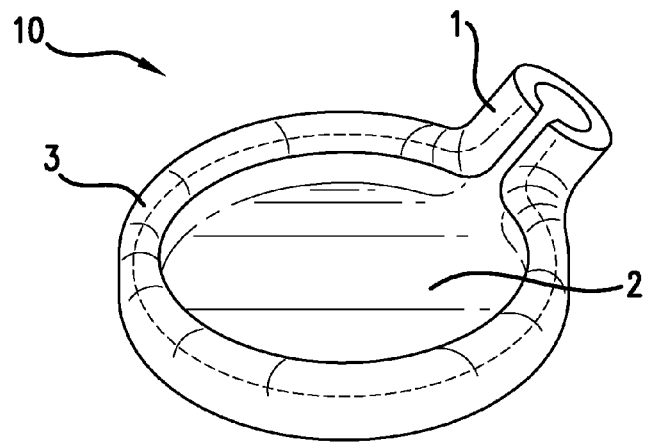
FIG. 1 is a perspective view of a mouth mirror cover with a bottom portion.

FIG. 1 shows a mouth mirror cover (10) with a bottom portion (1) when not attached to a mouth mirror (4). The back portion (2) that is generally round and planar completely covers the back of a mouth mirror (4) when attached. The side portion (3) which is curved is seamlessly connected to the back portion (2) and completely covers the sides of a mouth mirror (4) when attached. The bottom portion (1) completely covers the back and sides of the top of the handle (5) (5) of a mouth mirror (4) when attached. The handle (5) in all embodiments, may be various lengths and without effecting the function of the cover (10)

Figure 2:
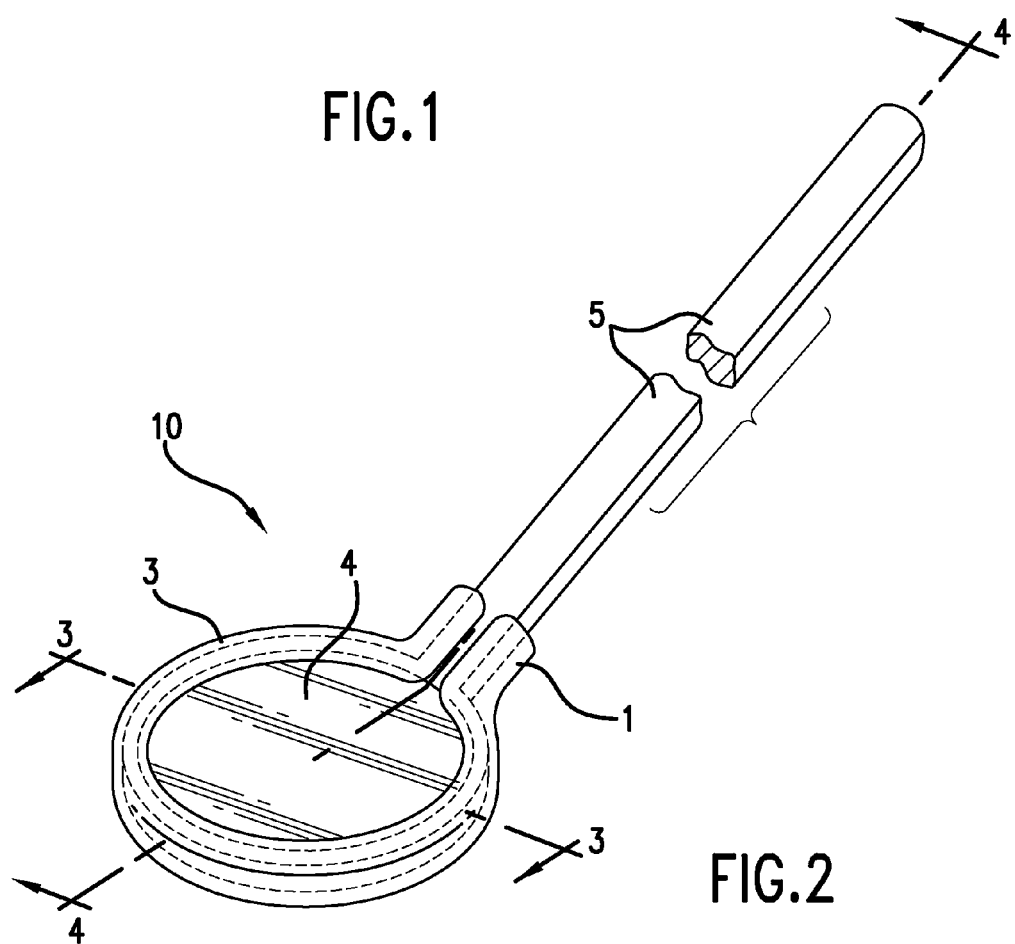
FIG. 2 is a perspective view of a mouth mirror cover with a bottom portion attached to a mouth mirror and handle (5).

FIG. 2 shows a mouth mirror cover with a bottom portion (1) when attached to a mouth mirror (4). The side portion (3) is shown to completely cover the sides of the mouth mirror (4) but not the mirror of the mouth mirror (4). As a result, the only part of the mouth mirror (4) left exposed when the mouth mirror cover (10) is attached, is the mirror. The bottom portion (2) covers all but a small front portion of the handle (5).

Figure 3:
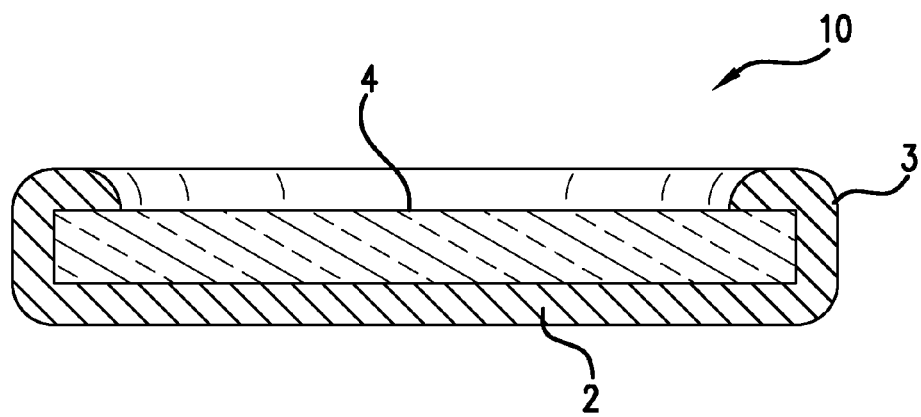
FIG. 3 is a cut away view of a mouth mirror with mouth mirror cover attached.

FIG. 3 shows a cut away view of a mouth mirror (4) with mouth mirror cover (10) attached. The back portion (2) covers the entire bottom side of the mouth mirror, and the side portion (3) covers the sides and the outer rim of the front of the mirror. Depending on the mouth mirror (4) it is covering, the mouth mirror cover (10) may cover a small portion of the outside edge of the mirror, for example, 10%. By covering the outer rim of the side portion, the mouth mirror cover's (10) ability to grip the mouth mirror (4) increases and the probability of the mirror contacting a person's mouth when it is in use decreases.

Figure 4:
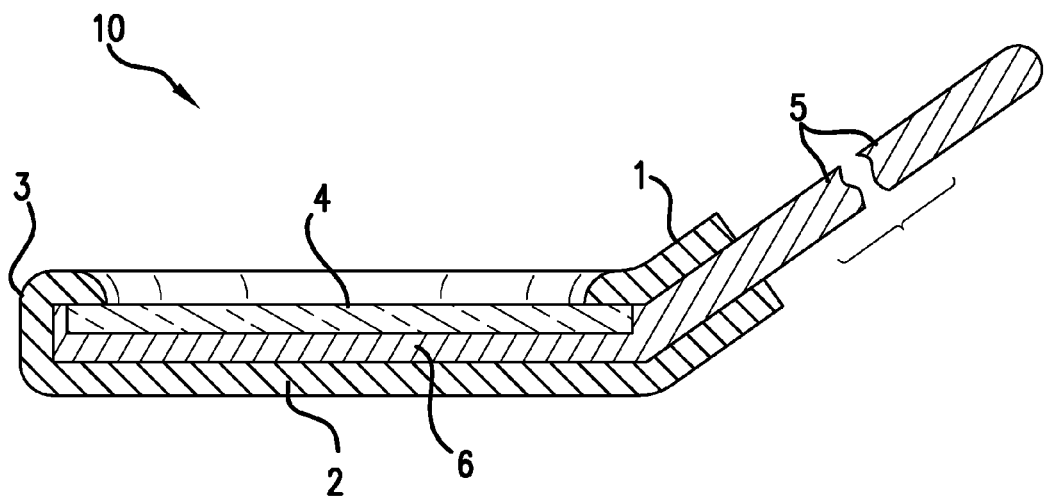
FIG. 4 is a cut away view of a mouth mirror and handle (5) with a mouth mirror cover attached.

FIG. 4 shows a cut away view of a mouth mirror (4) with mouth mirror cover (10) attached. The back portion (2) covers the entire bottom side of the mouth mirror (4), and the side portion (3) covers the sides and the outer rim of the front of the mouth mirror (4). The bottom portion (1) covers the top of the handle (5) of the mouth mirror (4).

Figure 5:
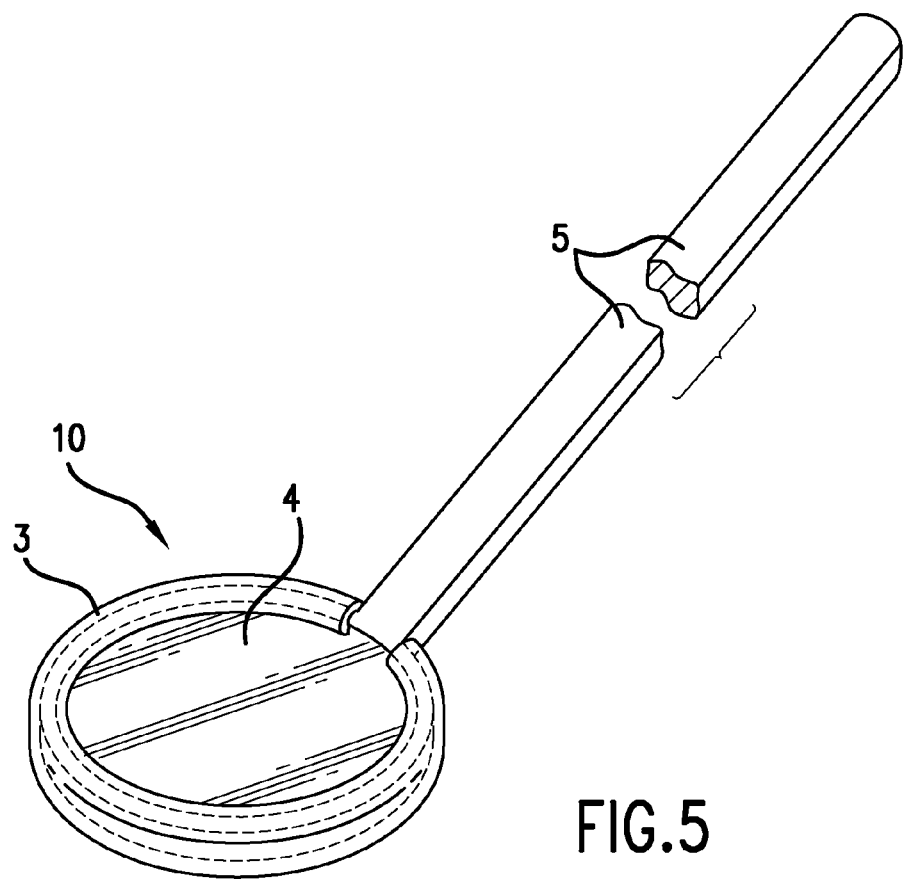
FIG. 5 is a perspective view of a mouth mirror cover without a bottom portion attached to a mouth mirror and handle (5).

FIG. 5 shows a mouth mirror cover (10) without a bottom portion when attached to a mouth mirror (4). The side portion (3) is shown to completely cover the sides of the mouth mirror (4) but not the mirror of the mouth mirror (4). The handle (5) portion is left completely exposed.

Figure 6:
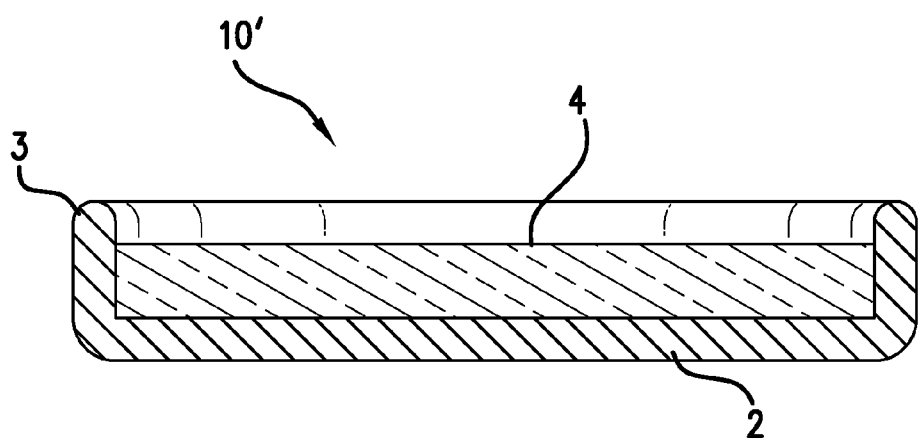
FIG. 6 is a cut away view of a mouth mirror.

FIG. 6 shows a cut away view of a mouth mirror (4) with mouth mirror cover attached (10'). The back portion (2) covers the entire bottom side of the mouth mirror (4), and the side portion (3) covers the sides but not the outer rim of the front of the mouth mirror (4). In this alternative embodiment the entire front face of the mouth mirror (4) remains uncovered. The side portion (3) protrudes above the rim of the front face of the mouth mirror (4) to reduce the probability that the mouth mirror will contact the mouth while in use.

In some embodiments, the device has a bottom portion (1) that conforms to at least a top portion of the handle (5) of a dental mirror wherein the bottom portion (1) does not completely wrap around the handle (5) portion. In this embodiment the bottom portion (1) completely covers the back and sides of the top of the handle (5) on the dental mirror but leaves a small portion of the middle of the front of the handle (5) uncovered. The back of the bottom portion (1) covers the back of the handle (5), the sides of the bottom portion (1) cover the sides of the handle (5), and the front of the bottom portion (1) partially covers the front of the handle (5). The front of the bottom portion (1) when fitted to the handle (5) extends from the sides of the bottom portion (1) on each side of the handle (5) to cover, but not completely cover, the front face of the handle (5). When fitting the device to a dental mirror the front of the bottom portion (1) of the device that will cover the front portion of the handle (5) is pulled back, the back of the handle (5) is placed against the back of the bottom portion (1) and the front of the bottom portion (1) is released allowing it to wrap around the front of the handle (5) on either side.

From the foregoing discussion, one skilled in the art can easily ascertain the essential characteristics of this invention and, without departing from the spirit and scope thereof, can make various changes and modifications of the invention to adapt it to various usages and conditions.

The invention claimed is:

1. A dental mirror apparatus cover comprising:
    A. a generally round and planar back portion suitable for covering a dental mirror frame and
    B. a curved side portion extending from the round and planar back portion with curved walls for extending over and around sides of a frame of a dental mirror and of a length suitable for securing said dental mirror cover to a frame of a dental mirror without obstructing a mirror surface of the dental mirror and wherein an inner surface of said cured side portion consists of a single curve or is flat and wherein said round and planar back portion and curved side portion comprise soft elastic material, and
    wherein portions A and B comprise one piece.

2. A dental mirror cover of claim 1 which is capable of covering the entire frame of a dental mirror.

3. A dental mirror cover of claim 1 which is capable of leaving at least 90% of the mirror surface of a dental mirror uncovered when attached to said dental mirror.

4. A dental mirror cover of claim 1 wherein the dental mirror cover can be sterilized without losing its shape.

5. A dental mirror cover of claim 1 wherein the dental mirror cover additionally comprises a bottom portion extending from the back portion, wherein said bottom portion comprises curved walls of a length that conforms to a handle of a dental mirror so as to partially cover said handle when said dental mirror cover is secured to a frame of a dental mirror.

6. A dental mirror cover of claim 5 wherein the bottom portion of said dental mirror cover is capable of extending the entire length of the handle (5) of the dental mirror.

7. A dental mirror cover of claim 1 which is capable of attaching to a dental mirror without covering any portion of the mirror surface of said dental mirror.

8. A dental mirror cover of claim 1 comprised of antimicrobial material.

9. A dental mirror cover of claim 1 wherein the inner surface generally conforms to the shape of the frame of a dental mirror.

\* \* \* \* \*